United States Patent
Piett et al.

(10) Patent No.: US 8,751,265 B2
(45) Date of Patent: Jun. 10, 2014

(54) LOCATION-BASED INFORMATION FOR EMERGENCY MANAGEMENT

(71) Applicant: Rave Wireless, Inc., Framingham, MA (US)

(72) Inventors: William T. Piett, Southborough, MA (US); Matthew A. Serra, Morristown, NJ (US); Noah J. Reiter, Boston, MA (US)

(73) Assignee: Rave Wireless, Inc., Framingham, MA (US)

( * ) Notice: Subject to any disclaimer, the term of this patent is extended or adjusted under 35 U.S.C. 154(b) by 0 days.

(21) Appl. No.: 13/760,711

(22) Filed: Feb. 6, 2013

(65) Prior Publication Data

US 2013/0203039 A1    Aug. 8, 2013

Related U.S. Application Data

(60) Provisional application No. 61/595,286, filed on Feb. 6, 2012.

(51) Int. Cl.
*G06Q 10/00* (2012.01)
*G06Q 50/00* (2012.01)
*G06Q 50/22* (2012.01)
*G06Q 50/26* (2012.01)

(52) U.S. Cl.
CPC ............... *G06Q 50/22* (2013.01); *G06Q 50/26* (2013.01); *G06Q 50/265* (2013.01)
USPC .............................................. 705/2; 705/325

(58) Field of Classification Search
None
See application file for complete search history.

(56) References Cited

U.S. PATENT DOCUMENTS

| 6,028,514 | A  | 2/2000  | Lemelson et al. |
| 6,189,029 | B1 | 2/2001  | Fuerst |
| 7,522,038 | B2 | 4/2009  | Edwards et al. |
| 7,602,277 | B1 | 10/2009 | Daly et al. |
| 7,617,287 | B2 | 11/2009 | Vella et al. |
| 7,685,245 | B1 | 3/2010  | Rodkey et al. |

(Continued)

FOREIGN PATENT DOCUMENTS

WO    2004/049198 A1    6/2004

OTHER PUBLICATIONS

Classapps, SelectSurvey.Net Training Manual, Feb. 24, 2012, classapps.com.*

(Continued)

*Primary Examiner* — Elaine Gort
*Assistant Examiner* — Jason Tiedeman
(74) *Attorney, Agent, or Firm* — Occhiuti & Rohlicek LLP (57) ABSTRACT

An apparatus for management of information for use in mitigating an emergency includes a data storage element configured to store registrant information obtained from members of a population residing in a particular geographic area and a set of survey questions, and a data storage system, the data storage system being programmed to implement a survey editor for enabling an emergency management official to create a survey for soliciting information from the members for inclusion in the registrant information, the survey editor providing, to the emergency management official, an interface for selecting a subset of questions from the set of questions, the subset of questions being selected from the set of questions based at least in part on the particular geographic area, and a survey portal for receiving, from the member, a response to the survey for integration into the reference data.

17 Claims, 4 Drawing Sheets

(56) References Cited

U.S. PATENT DOCUMENTS

| | | |
|---|---|---|
| 7,756,829 B2 | 7/2010 | Bhanote |
| 7,949,548 B2 | 5/2011 | Mathai et al. |
| 8,190,118 B2 | 5/2012 | Sennett et al. |
| 8,255,978 B2 | 8/2012 | Dick |
| 8,306,503 B2 | 11/2012 | Morrison |
| 2002/0059246 A1 | 5/2002 | Rowe |
| 2006/0089861 A1 | 4/2006 | King et al. |
| 2007/0275690 A1 | 11/2007 | Hunter et al. |
| 2008/0010687 A1 | 1/2008 | Gonen et al. |
| 2008/0085696 A1* | 4/2008 | Salahshour et al. ....... 455/404.1 |
| 2008/0215626 A1* | 9/2008 | Gomez ..................... 707/104.1 |
| 2008/0288271 A1 | 11/2008 | Faust |
| 2009/0172131 A1 | 7/2009 | Sullivan |
| 2010/0135471 A2* | 6/2010 | Hulls .............................. 379/37 |
| 2012/0028599 A1 | 2/2012 | Hatton et al. |
| 2012/0185897 A1 | 7/2012 | Gould et al. |

OTHER PUBLICATIONS

Malizia et al. "SEMA4A: An ontology for emergency notification systems accessibility" (Apr. 2010) Retrieved from: http://www.sciencedirect.com/science/article/pii/S0957417409008768.

White et al. "An Online Social Network for Emergency Management" (May 2009) retriueved from: http://www.iscramlive.org/ISCRAM2009/papers/Contributions/163_An%20Online%20Social%20Network%20For%20Emergency_White2009.pdf.

* cited by examiner

LOCATION-BASED INFORMATION FOR EMERGENCY MANAGEMENT

RELATED APPLICATION

This application claims the benefit of the priority date of U.S. Provisional Application 61/595,286, filed on Feb. 6, 2012, the content of which is herein incorporated by reference.

FIELD OF DISCLOSURE

This disclosure relates to mitigating casualties and property damage resulting from disasters, such as terrorist attacks, and in particular, the management of information for planning and use of emergency response systems.

BACKGROUND

A terrorist attack poses a significant threat to public safety. Aside from casualties caused by the event itself, there may be collateral damage as a result of the attack's aftermath. For example, damage to urban infrastructure may cut essential services, such as water and electricity, to certain parts of the city. An attack on a dam or nuclear facility may require evacuation of selected portions of an urban area.

Responsibility for planning responses to such incidents, as well as for execution of such responses, typically falls on various emergency management agencies. These agencies have different jurisdictions. Some are responsible for a city. Others are responsible at a state or county level. Others, such as FEMA, are responsible on a nationwide scale.

To mitigate casualties as a result of such incidents, it is useful to provide these agencies with information about the residents of particular geographic areas. For example, if electricity is cut to a certain district of the city, it may be useful for an emergency management agency to know which residents of that district, if any, rely on electrically powered medical equipment. Such information would enable the emergency management agency to evacuate those residents first.

Another example of information that is useful in planning emergency response is information about pets in a particular geographic area. While information about pets might seem of little consequence, it has been found that those who resist evacuation often do so because they discover that they cannot bring their pets to a shelter with them. Thus, in planning the locations of emergency shelters near a zone, such information would enable the emergency planners to include appropriate pet care facilities for any shelters intended for evacuation of residents in that zone. This in turn would encourage compliance with an evacuation order and thereby reduce casualties, thus mitigating damage associated with a terrorist attack.

In practice, however, there is no systematic way of acquiring, disseminating, and updating information of this type.

Timely and effective planning and response to emergencies thus depends on accurate and easily accessible information. Emergency management agencies charged with mitigating the effects of an emergency as well as reacting to incidents require a clear picture into the risks associated with the incident itself and with the various options available for mitigating the damage resulting from the incident. There is an increasing recognition that having access to timely and accurate information can increase the accuracy and speed of decisions, thereby improving the incident outcome. GIS ("Geographic Information Systems"), ALI (Automatic Location Information) databases, basic opt-in user portals for emergency notification systems, paper based systems, or simple databases of localized information and other similar tools have been developed to provide such information to public safety agencies.

A number of attempts have been made to collect information from the general population in support of emergency management or emergency preparedness activities. These systems tend to reside locally within a particular public safety answering point ("PSAP") or a particular emergency management organization. As such, these systems are managed solely by these resources and not available to others that might be called upon to assist in a large scale disaster.

Other systems are made available to the general public via the internet. Examples of such systems include, the New Jersey special needs registry, the Broward County, Florida vulnerable population registry, the Utah special needs registry, the Clay County, Minnesota vulnerable population registry, the Fargo, N. Dak. vulnerable population registry, the Kansas vulnerable needs planning system, and the Wilkin County Minnesota vulnerable population registry.

SUMMARY

The invention relies in part on the recognition of a need to provide emergency managers with one or more of the following capabilities: the ability to acquire generalized data that can be tailored to the needs of a specific geography, the ability to filter information presented to emergency managers based on incident geography or incident type, to guide members of the population, or other data sources, through a data collection procedure that depends on such local factors as geography, localized risk, or the public safety agency's policies and procedures, the ability to provide effective mechanisms to keep such data up-to-date, the ability to support proactive incident intervention instead of only providing information when a resident places an explicit request for assistance (e.g., dials 9-1-1), the ability to easily allow for cost effective maintenance of dynamic data that can frequently change, the ability to provide regional reporting and permissions-based reporting, and the ability to manage large-scale events, such as hurricanes, that cross many jurisdictional boundaries by aggregating data collected by local and regional emergency management agencies.

The invention described herein provides an emergency information system that can be used by public safety agencies to create and disseminate surveys for soliciting and collecting data about selected subsets of their respective constituencies. These surveys allow public safety agencies to structure data collection to maximize the relevancy of the data collected from the population. Among the advantages found in different embodiments of this invention is the provision of one or more services such as collecting specific information from the community, or through aggregation of third party sourced data, the provision of a way for public safety agencies to specify survey questions that are tailored to the emergency management needs of a specific geographic location, with the geographic region defining a specific survey possibly corresponding to the public safety agency's jurisdiction, a subset of that jurisdiction, or an area spanning multiple jurisdictions, the provision of a way for the public safety agency to query the database for information relevant to any geographic area of interest, event type, survey question response, or other data identifying a set of survey respondents, and the provision of tools to further visualize, interpret, and act on the information returned by such a query.

A system as described herein can include one or more of an administrative module, a survey editor, a survey portal, a data store and its associated interfaces, and a business intelligence platform.

The administrative module defines the geographic jurisdiction of a given user of the system, for example a public safety agency. It also defines those tools needed to manage a user's authority to modify, query, view, and act on collected registrant information. The administrative module thus defines credentials for different users and manages access to the registrant information based on those credentials.

The survey editor allows a public safety organization to design surveys that are relevant to its jurisdiction or geographic regions of interest, to localized risks, and to the public safety organization's own response capabilities.

The survey portal presents a survey to members of a community. The survey questions of this survey are custom tailored to the community members' locations, and preferences. In some cases, the survey is an adaptive survey in which a question may depend on the community member's answers to preceding survey questions.

The data-store holds the collected registrant information, provides a number of interfaces. These interfaces control access to that registrant information, and enable information exchange via various formats and technologies.

The business intelligence platform allows public safety agencies to issue real-time queries against the collected registrant data, including data that identifies a registrant, such as a telephone number or an address, data relevant to an incident type, data identifying a registrant's current location or the locations that the registrant is most likely to frequent, and the registrant's answers to survey questions. Thus, the business intelligence platform would permit queries asking for a list of all registrants who live in a flood plain, or those who are homebound. The business intelligence platform also provides tools to act upon data returned by queries. These tools include functions for displaying results in graphical or tabular form, interactive maps, tools to simplify collaboration with others and to share the results of the business intelligence platform, tools to make data available to external systems, and tools to initiate communications with the affected citizens via, for example, a bilateral pointcaster.

In the system and method described herein, registrant information is not constrained by geography from the outset. Instead, it is warehoused in a national or regional database and geographically filtered. The warehousing of registrant information in a national or regional database allows for changes in public safety jurisdiction without requiring data migration or retraining the population. In addition, data collected can be easily modified to reflect the needs of a particular public safety agency or geography. The correct data collection form is presented dynamically to prospective registrants based on their location. Another advantage of at least some of the systems and methods described herein is that data collection is not constrained to a specific population or demographic group. This allows public safety officials to collect and analyze information for all segments of the population, thus conforming to FEMA's "whole community preparedness" guidelines. Yet, another advantage of at least some of the systems and methods described herein is that the data collection process does not rely on public safety agency personnel to manually enter data provided by members of the public into local databases, and/or to manage manual processes to keep the data up-to-date.

In one aspect, the invention features a computer-implemented method comprising forming a survey, using a survey editor of a survey system, including accessing a survey database, and selecting a subset of a plurality of survey questions stored in the survey database, at least one profile attribute associated with each of the plurality of survey questions, and enabling personalized selection of at least one of the subset of survey questions according to the associated profile attribute.

In some practices, the method also includes configuring a survey module according to the results of the personalized selection.

Other practices include conducting a survey of a registrant, at least one profile attribute being associated with the registrant. Among these practices are those in which enabling personalized selection of at least one of the subset of questions includes selecting a survey question based on the profile attribute of the survey question and the profile attribute of the registrant. These practices also include implementations in which conducting a survey includes presenting the selected survey question to the registrant.

Other practices include an additional step of receiving an input from a client via the survey editor interface, the input characterizing a target profile attribute. In some of these practices, conducting a survey of the registrant includes conducting the survey if the profile attribute associated with the registrant matches the target profile attribute.

Yet other practices include receiving an input from the registrant representative of a response to the selected survey question, and storing the response in a registrant database in association with a profile associated with the registrant. Among these practices are those that also include requesting, from the registrant, consent to allow access to the stored response. Also among these practices are those in which the registrant database includes registrant data associated with a plurality of clients of the survey system. Some of these practices also include enabling authorized access, by a second client, to first registrant data associated with a first client.

In some practices, the profile attribute is a geographic attribute. In others, the profile attribute is a demographic attribute. In yet other practices, the profile attribute is a response to a previously presented survey question.

Some practices of the invention also include receiving an input from a registrant via a user interface, the input being representative of a geographic attribute of the registrant, and storing the input in a registrant database as a geographic profile attribute associated with the registrant Practices of the invention also include those in which the geographic attribute includes a geographic point relevant to the registrant, those in which the geographic attribute includes a geographic boundary relevant to the registrant, and those in which the geographic attribute includes a civic address associated with the registrant.

Also among the practices of the invention are those in which enabling personalized selection of at least one of the subset of survey questions includes selecting a survey question based on the geographic profile attribute In yet other practices, enabling personalized selection further includes selecting the survey question based further on a response of the registrant to a previously presented survey question.

Among the additional practices of the invention are those in which the survey database is located at a location different from a location of a client of the survey system, and also those in which the survey database includes data associated with a plurality of clients of the survey system.

Some practices include receiving a new survey question from a client via the survey editor interface, and adding the new survey question to the survey database.

Other practices include monitoring a profile associated with the registrant, and in response to a change in the profile, enabling personalized selection of at least one of the subset of survey questions based on a changed profile attribute associated with the registrant.

Yet other practices include sending a reminder to the registrant. The reminder can be a reminder to update a profile associated with the registrant or a reminder to respond to a survey question.

In another aspect, the invention features an apparatus for management of information for use in mitigating an emergency. Such an apparatus includes a data storage element configured to store registrant information obtained from members of a population residing in a particular geographic area and a set of survey questions, and a data storage system, the data storage system being programmed to implement a survey editor for enabling an emergency management official to create a survey for soliciting information from the members for inclusion in the registrant information, the survey editor providing, to the emergency management official, an interface for selecting a subset of questions from the set of questions, the subset of questions being selected from the set of questions based at least in part on the particular geographic area, and a survey portal for receiving, from the member, a response to the survey for integration into the reference data.

In some embodiments, the data storage system is further configured to implement a business intelligence platform for receiving instructions from an emergency management official for identifying a subset of the registrant information based at least in part on a registrant profile that includes a geographic location, and retrieving the subset of the registrant information. Among these embodiments are those in which the business intelligence platform is configured to inspect credentials of the emergency management official and to control access to the registrant information based at least in part on the credentials. Also included are embodiments in which the business intelligence platform includes an interactive map interface for receiving, from the emergency management official, a graphical representation of the particular geographic area.

Also among the embodiments are those in which the data storage system is further configured to implement a point-caster configured to send emergency messages to selected members of the population based on both geographic location of the members as specified in the registrant information and matching an element of the subset of questions being selected. Among these embodiments are those in which point-caster is further configured to receive response messages from the selected registrants in response to the emergency messages.

In yet other embodiments, the data processing system is further configured to provide access to the registrant information to a call-taker of a 9-1-1 call. Among these embodiments are those in which the data processing system is further configured to restrict access to selected portions of the registrant information based at least in part on credentials of the call-taker.

A variety of ways are available to configure the survey editor. For example, in some embodiments, the survey editor includes an interface for receiving a free-form question and including the free-form question in the survey with the subset of questions. In others, the survey editor includes an interactive map interface for receiving, from the emergency management official, a graphical representation of the particular geographic area. And in yet others, the survey editor is further configured to inspect credentials of the emergency service official and to restrict survey editing by the emergency service official based at least in part on the credentials.

The apparatus described herein can be used in a number of emergencies. For example, in some cases, the emergency is a result of a terrorist attack. However, the emergency can also be another man-made emergency, or a natural emergency, such as an earthquake, tornado, a hurricane, a tsunami, a meteor strike, a hurricane, a massive disruption of electrical service or service by another utility. In some cases, the service may be used in the event of a large scale military invasion. For example, in defense of homeland security, the service may be commandeered by the National Guard, or by the Army.

In yet other embodiments, the data processing system is configured to interact with a first emergency management official and with a second emergency management official, and wherein the data processing system is further configured to deny access to selected registrant information to the first emergency management official and to grant access to the selected registrant information to the second emergency management official.

These and other features of the invention will be understood from the following detailed description and the accompanying figures, in which

DETAILED DESCRIPTION

Figure 1:
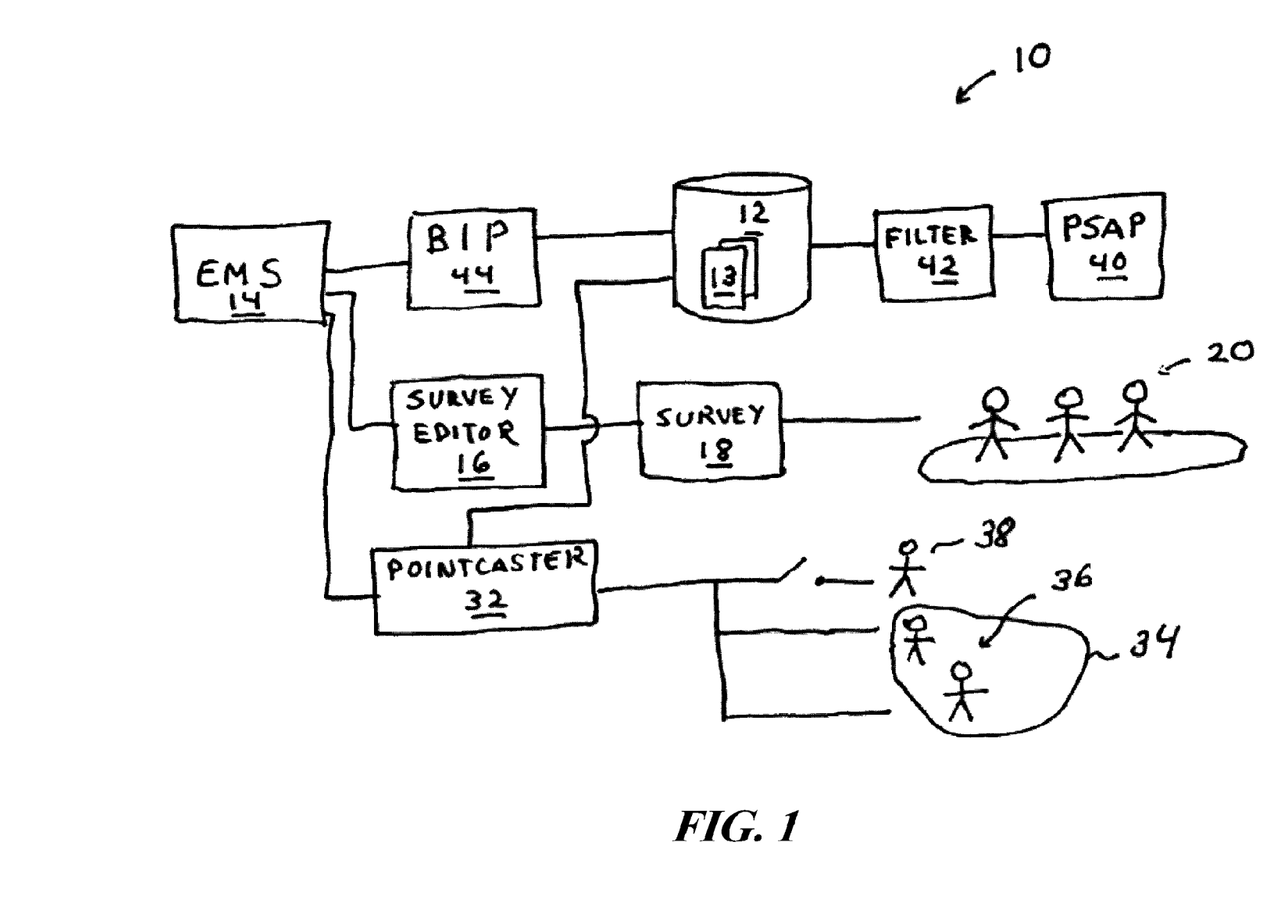
FIGS. 1 and 4 show emergency information systems.

Referring to FIG. 1, an emergency information system 10 includes an emergency information data store 12 that contains registrant information 13 about those members of the public who have chosen to provide such information to an emergency management agency.

An emergency management official 14, who works on behalf of an emergency management agency, interacts with a survey editor 16 to construct a survey for soliciting information from the public for collecting and maintaining registrant information 13. This survey is provided to a survey portal 18 accessible via the Internet by any member of the public 20 within a particular geographic area. A member of the public who fills out a survey will be referred to herein as a "registrant."

Figure 2:
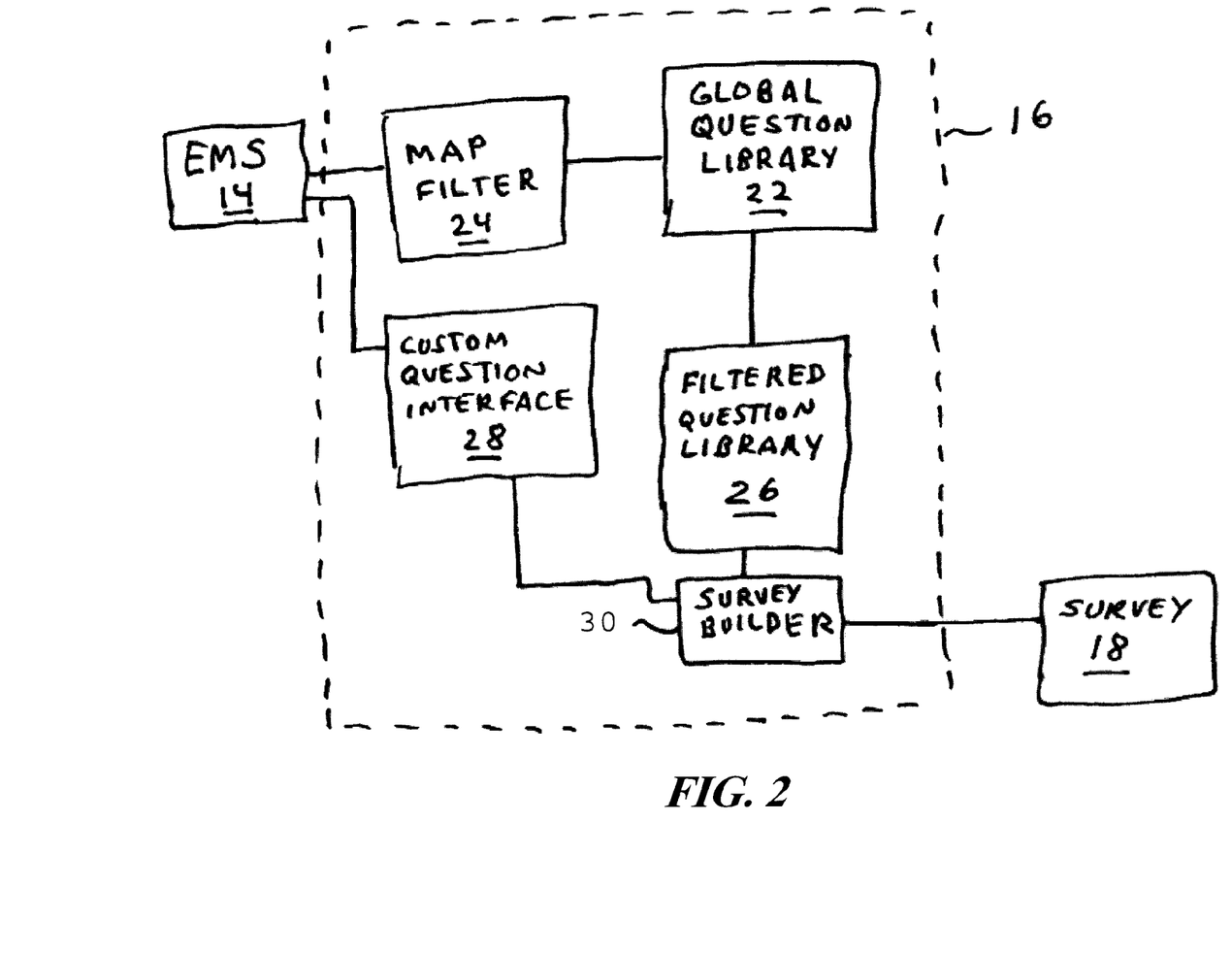
FIG. 2 shows details of a survey editor for the system shown in FIG. 1.

The survey editor 16, shown in more detail in FIG. 2, features a global question library 22 containing questions that can be assembled to form a survey for acquiring and maintaining the registrant information 13.

In the illustrated embodiment, the emergency management official 14 does not access the global question library 22 directly. Instead, the emergency management official 14 uses a map filter 24 to specify the geographic area, or zone, that contains a population from which the survey is intended to solicit information. The map filter 24 uses this information to select, from the global question library 22, those questions that are deemed appropriate to the particular zone. These questions are included in a filtered question library 26 that is then made accessible to the emergency management official 14. The emergency management official 14 then selects questions from the filtered question library 26 for inclusion in the survey.

In many cases, it is not possible to anticipate all the possible questions that might be asked on a survey. To avoid constraining the emergency management official 14, the survey editor 16 also provides a custom question interface 28 for composing survey questions that may not have been included as part of the filtered question library 26.

The selected questions from the filtered question library 26 and any composed survey questions from the custom question interface 28 are provided to a survey builder 30, the output of which is a survey to be made available to the public via the survey portal 18.

Survey questions typically solicit registrant information 13 that would be useful in making arrangements for necessary resources prior to a disaster, as well as deploying resources during and in the aftermath of a disaster. Such registrant information 13 would include, for example, information about the number of residents in the household, which would be useful for planning shelters for evacuation. Registrant information 13 could include health conditions of the registrant, medications being taken, blood type, and other medical information. This type of registrant information 13 would be useful for deciding what medical supplies should be stockpiled in the shelter serving the registrant, or for determining that a registrant might need assistance with emergency evacuation due to either a physical or social limitation. The registrant information 13 can also include information on food and water supplies, thus providing the emergency management official 14 with a sense of how quickly food and water need to be delivered to an affected zone. Other examples of registrant information 13 include photographs of family members, to assist in identifying missing persons and/or fatalities, and information about the pet and livestock population, to assist in planning animal care facilities at evacuation shelters or alternate locations.

The registrant information 13 typically includes emergency contact information, such as email addresses and telephone numbers, that can be used by the emergency management official 14 to send messages to selected registrants 20. Referring back to FIG. 1, the emergency management official 14 does this by specifying, to a bilateral pointcaster 32, a geographic zone 34 and message text. The message text can be selected from a menu of pre-defined messages. Alternatively, the message text can be a custom message composed by the emergency management official 14.

The bilateral pointcaster 32 then retrieves the emergency contact information from the registrant information 13 for those registrants 36 within the specified geographic zone 34. It then automatically contacts those registrants 36 and omits contacting those registrants 38 that are outside the zone 34 or those who did not meet certain survey criteria.

For example, if a terrorist attack or other event were to compromise a nuclear power plant, the emergency management official 14 would be presented with a map centered on the nuclear power plant. He would then define a two-mile radius around the power plant on this map and specify the circular region thus defined to the bilateral pointcaster 32, together with a list of shelters for evacuees. The bilateral pointcaster 32 could then retrieve, from the data store 12, emergency contact information for all registrants within a two-mile radius, inform them of the evacuation, and direct them to an appropriate shelter. This mass notification procedure can be done much more rapidly than the traditional method, which may involve having a truck driving up and down the streets of the affected area with a bullhorn, or which may involve broadcasting instructions by mass media in the hope that enough people are listening to cause an effective evacuation.

The bilateral pointcaster 32 is also configured to communicate in the other direction. Thus, each registrant 38 in an affected zone 38 could send a message back via the bilateral pointcaster 32 reporting that he and his family have evacuated the neighborhood as requested and have arrived at a designated shelter.

As evacuation proceeds, the emergency management official 14 receives a stream of updated data. Using this data, the emergency management official 14 can monitor the evacuation procedure as it unfolds. In doing so, the emergency management official 14 can observe any irregularities and dispatch resources that may be used to correct those irregularities.

Registrant information 13 is also available to a 9-1-1 call-taker at a public safety access point 40. As a result, when a registrant 38 uses a calling number to make a 9-1-1 emergency call, the registrant information 13 in the data store 12 can be used to link the calling number to a particular registrant. The 9-1-1 call-taker will thus have selected information about the registrant, who is presumably the caller.

To maintain privacy, and to avoid cluttering the display with extraneous information, the registrant information 13 is passed through a credential filter 42 before being presented to the 9-1-1 call-taker 40. The credential filter 42 receives a credential as input and decides, based on that credential, what subset of the registrant information 13 can be released. As a result, when the 9-1-1 call-taker 40 presents a credential, the credential filter 42 passes only that subset of the registrant information 13 that is necessary for responding to the 9-1-1 call.

The emergency management official 14, like the 9-1-1 call-taker 40, also has access to the registrant information 13 in the data store 12. However, unlike the 9-1-1 call-taker 40, who only receives registrant information 13 when the registrant calls, the emergency management official 14 can actively query the data store 12 using a business intelligence platform 44.

Figure 3:
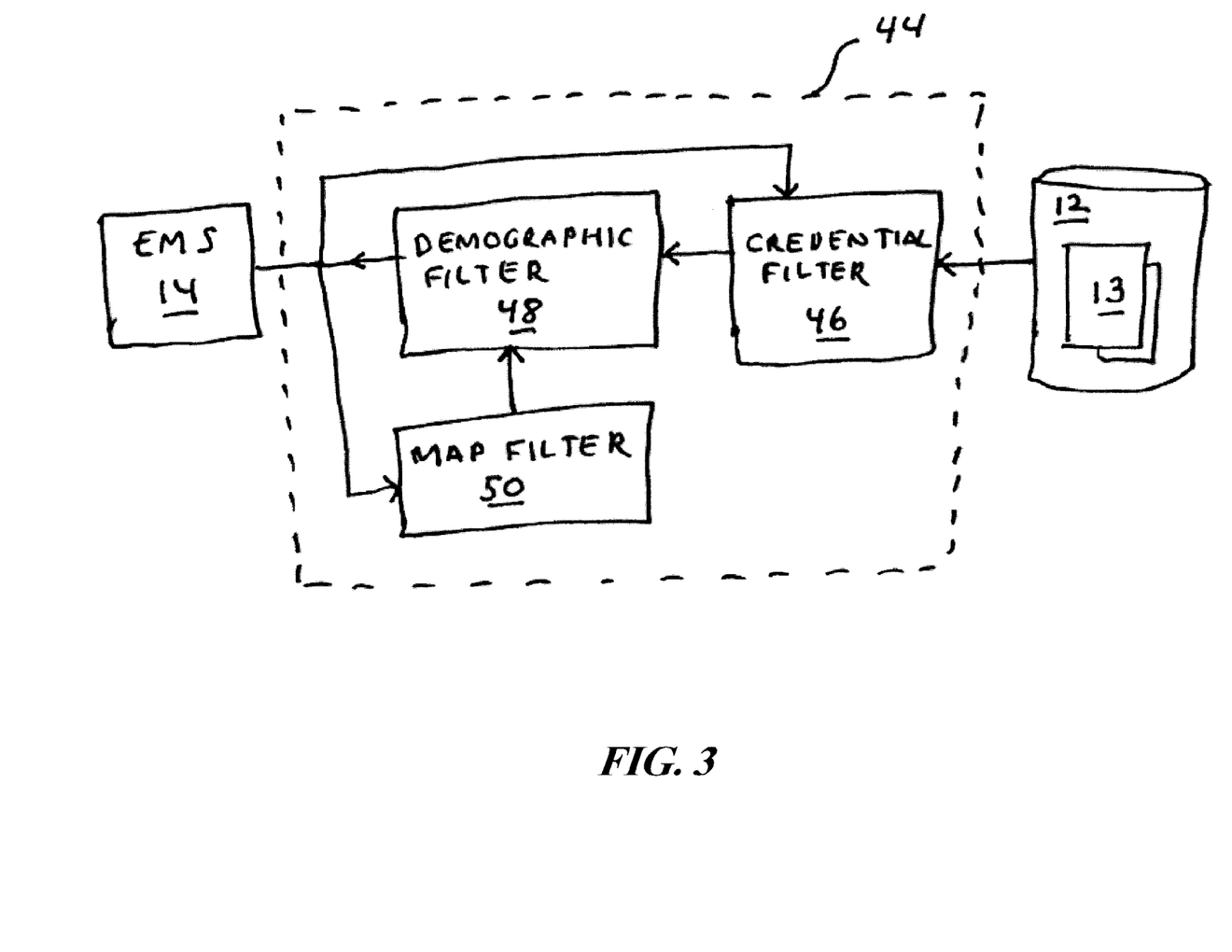
FIG. 3 shows details of a business intelligence platform for the system of FIG. 1.

As shown in FIG. 3, the business intelligence platform 44 includes a credential filter 46 that controls what registrant information 13 is available to a particular emergency management official 14. A credential filter 46 is useful because different emergency service agencies with different jurisdictions will need access to registrant information 13 concerning different subsets of the registrants. For example, an emergency service agency charged with public safety for a county will generally not need statewide or province-wide registrant information.

The credential filter 46 also provides a way to protect registrant privacy when necessary by blocking access to certain types of registrant information 13. For example, emergency planners who are responsible for planning the number of beds in a shelter will not need photographs of family members to do so. On the other hand, search-and-rescue personnel might find such photographs very useful, but would most likely not need to know, for example, that a particular registrant relies on a dialysis machine.

The business intelligence platform 44 also includes a demographic filter 48 to allow the emergency management official 14 to identify all registrants that have a common profile. A suitable interface for the demographic filter 48 would present the emergency management official 14 with a series of check boxes. The set of all check boxes checked by the emergency management official 14 in that case would define an official-defined profile. The demographic filter 48 would then present information only about those registrants that satisfy that official-defined profile.

The business intelligence platform 44 also includes a map filter 50 that allows the official to dynamically define a geographic region by simply drawing the region on an on-screen representation of a map. The output of the map filter 50 is used to extract registrant information 13 only for those registrants that satisfy the official-defined profile, as specified through the demographic filter 48, and that also reside within the geographic region defined by the emergency management official 14 using the map filter 50.

Figure 4:
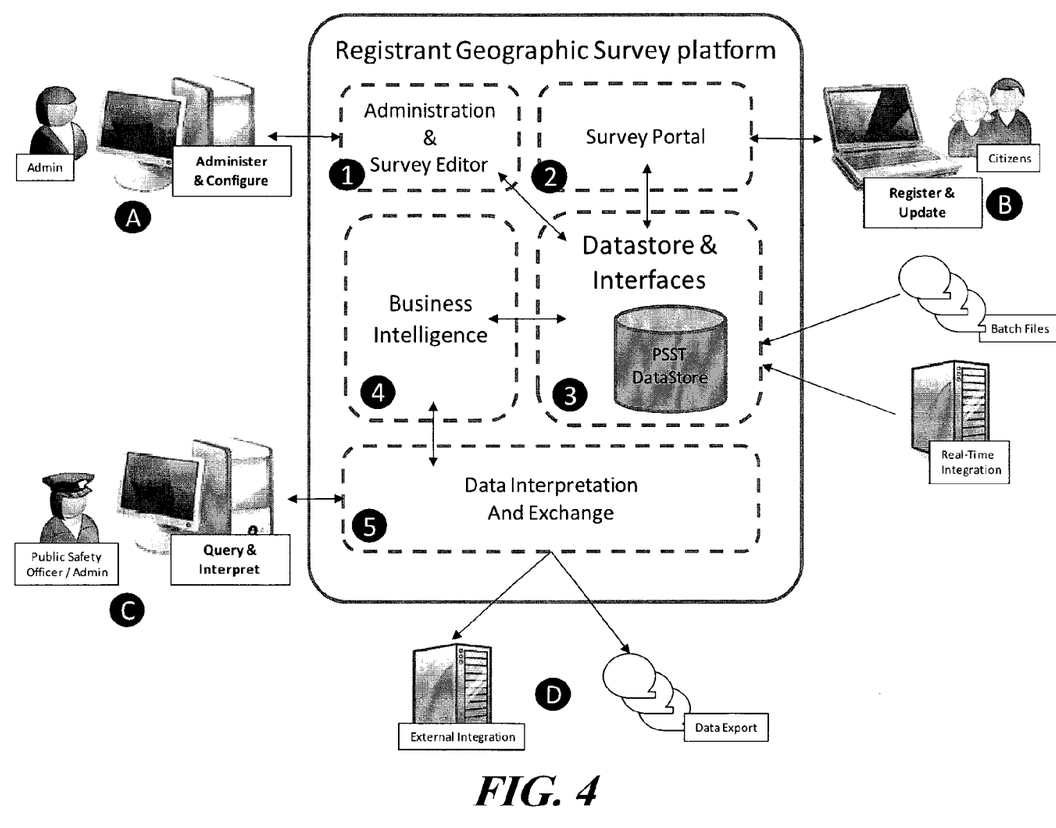

Another embodiment, shown in FIG. 4, shows a registrant geographic survey platform having an administration and survey editor 1 in communication with an administrator A operating administration and configuration software, a survey portal 2 in communication with citizens B of the jurisdiction of the emergency management agency, a data-store 3 in data communication with both the survey portal 2 and the administration and survey editor 1 through respective associated interfaces, a business intelligence module 4 in communication with the data-store 3 over an associated interface, and a data interpretation and exchange module 5 in communication with the business intelligence module 4 and accessible by public safety officers and administrators C executing query and interpretation software, as well as with an external integration system D to which it can export data as needed.

The administrative modules, which are carried out by the administration and survey editor 1, support two kinds of administrators A: system administrators and public safety agency administrators.

System administrators manage global systems configurations and identify new public safety organizations that are to be granted access to the registrant information 13. Public safety agency administrators configure registrant geographic surveys to best suit their public safety agency's needs. They also execute queries against the registrant information 13, and take action based upon the outputs of these queries.

Both the system administrator and the agency administrator have their respective tool sets.

The system administrator's toolset includes a tool for adding, deleting, or editing survey questions that are to be made available to all public safety organizations for their use. These globally available questions are stored in the global question library 22.

The system administrator's toolset further includes tools for configuring an extent to which a public safety agency accesses the registrant information 13, typically by providing suitable credentials. These public safety agency administration functions include specifying a new public safety organization, identifying the geographic area served by the organization, and providing agency administrator accounts that are used by the public safety agency to access and configure the registrant information 13 for their needs.

The agency-administrator's toolset includes a tool for creating additional report administrators. These report administrators are privileged users who are able to view survey configurations, to execute queries against registrant information 13, and to take action based on the outputs of these queries.

The survey editor 1 allows a given agency administrator A to deem certain profile attributes and questions to be of interest to the public safety agency. Through the survey editor 1, an agency administrator is able to view all survey questions that are currently active within the public safety agency's jurisdiction. These survey questions are created by others in the public safety agency, or by other agencies that may have jurisdiction that overlaps that of the agency. Such questions are stored in the global question library 22.

The survey editor 1 also enables the agency administrator to do any one or more of the following: edit or remove an existing survey question active within the public safety agency's jurisdiction, to select a global survey question, or an existing registrant information attribute for inclusion in the agency's survey, to identify a new survey question of interest to the public safety agency, to identify the geographic area that is applicable to the new survey question, and to ensure that the survey question is presented only to those registrants within the specified geographic area, to identify valid answers for the survey question and/or to provide a way to receive an open-ended answer, to determine if the survey question should always be posed, or whether posing that question should be contingent upon the answer to a preceding survey question, and to determine if a particular survey question must be answered as a prerequisite to answering other questions in a survey.

The survey editor 1 is used by system administrators A to create, edit, and delete globally available survey questions stored in the global question library 22 and that are made available to all agency administrators for use within their local surveys.

The survey portal 2 includes a user-interface that allows citizens B to provide self-describing information in an effort to better inform public safety agencies serving their community. The survey portal 2 may be a standalone application, or it may be integrated with other data collection toolsets, such as those used to support registration for other community services, emergency notification, 9-1-1 databases, or town services. Additionally, the survey portal 2 could be integrated with other commercial systems, such as systems that provide various utilities or communications services, as an opportunity to encourage participation in the survey.

Upon reaching the survey portal 2, a citizen B establishes an account, and provides information about the civic addresses or locations that he is most likely to frequent. For example, a citizen B may provide information about their work, home, and vacation addresses, or a country club, health club, a church, a casino, or a nightclub that he frequents.

Based on one or more of the foregoing addresses, the survey portal 2 presents a set of questions to the citizen B. The citizen B, now a prospective registrant, will then answer these presented questions. Typically, the survey will pose questions related to the citizen's address, other members of his household, pets, vehicles, and emergency contacts. Any question deemed of value to the public safety agency can be asked.

As part of participating in the survey, the citizen B is informed of how any information that he provides will be used by the requesting public safety agency C. Additionally the survey invites the citizen's consent to share the provided survey information with public safety agencies C.

In some implementations, the survey portal 2 is integrated with other data collection functions. For example, collected registrant information 13 can be used to create a profile that can be shared with 9-1-1 call takers when the registrant places a 9-1-1 call from a recognized telephone number. In these cases, profile attributes may also be flagged for inclusion as part of the public safety organization's survey.

The survey portal 2 permits a citizen B, who, having registered can now be called a registrant, to revisit it later. In this case, the registrant logs back into the survey portal 2 using credentials created during initial registration. Upon logging back in, the registrant has an opportunity to respond to new or updated survey questions, to add to or modify aspects of their profile, and to answer any additional survey question that result from changes to the registrant information 13, or changes in the survey itself. For example, if the registrant's household size increases, the survey portal 2 will present new survey questions to solicit information about the new member of the household.

There is no guarantee that a registrant will take the trouble to log into the survey portal 2 when some event occurs that would require a change in that registrant's corresponding registration profile 13. In recognition of this, the survey portal 2 includes tools that remind registrants to revisit the survey portal 2 to confirm, and if necessary, to update the accuracy of the registrant information 13.

Reminders can include any combination of text-based messages, email, or voice notifications. The survey portal 2 sends these messages in response to some pre-defined triggering event. These triggering events can include, for example, lapse of some pre-defined interval since the registrant information 13 was last updated, or acquisition of data from a third party indicating, for example a change in a telecommunications account associated with the profile, or a transaction related to an address associated with a registrant through the registrant information 13.

The data store 3 retains both registrant information 13 and any data provided by an administrator A for future activities. Such activities include not only queries as issued through the business intelligence platform 4, but creation of and updates of registrant information 13, survey questions stored in the global question library 22, stored queries, and data that defines a public safety organization, such as its jurisdictional and administrator information.

The data store 3 has associated interfaces for enabling the survey editor 1 and the survey portal 2 to maintain the data stored therein. These interfaces also enable the business intelligence platform 4 to execute queries on data stored in the data store 3, and to retrieve results of such queries. Interfaces also permit validating the identities and authority of a given user who is attempting to access data to confirm that the user is indeed authorized to access the requested data.

The interfaces to the data store 3 also enable collection of information from external automated data sources. These interfaces can operate either in near-real-time, with immediate transactional updates, or in batch mode, in which data is processed in aggregate. The data source and data format can come from anywhere and are limited only by the capabilities of the interface.

The business intelligence platform 4 maintains the tools necessary for analysis of information provided by registrants or third parties. These tools include the ability to query the registrant information 13 that exists within a public safety agency's jurisdiction. Based on the public safety agency's needs, the agency administrator A or a public safety officer B can query the registrant information 13 to return a list of registrants and/or registrant addresses meeting the query's associated criteria.

The query criteria are established in advance, or configured ad-hoc. By establishing query criteria in advance, the public safety agency can be prepared to execute queries that address specific anticipated scenarios. For example, a query might be established in advance to return information about all citizens B who have identified themselves as requiring transportation should a region need to be evacuated.

Established query criteria can also be modified in real time to add time-sensitive information to a saved query containing criteria established in advance. For example, at the time of an incident, an agency administrator A could select an existing query that would return a list of registrants and associated addresses that are dependent on electrically powered medical devices. The agency administrator A could then further augment this query to identify a particular geography affected by a power outage. As a result, the agency administrator A would be able to create an actionable list of registrants and addresses that should receive prioritized attention, and a map display showing locations of their addresses.

Finally, queries may also be fully developed in real-time to support a response to unforeseen needs. For example, in the event that a terrorist attack on a dam threatens to unleash a flood in a low-lying area downstream, an agency administrator A could query the registrant information 13 for contact information associated with community members who have volunteered to make their earth-moving equipment available in the event of an emergency.

The data interpretation and exchange module 5 of the emergency information system 10 provides tools for visualizing and acting upon the information returned in response to queries made by the business intelligence platform 5.

Among the tools provided by the data interpretation and exchange module 5 is a viewer for viewing selected registrant information 13 associated with all registrant profiles meeting the query criteria specified by the business intelligence platform 5.

Also among the tools provided by the data interpretation and exchange module 5 is a map interface for visualizing the output of a query made by the business intelligence platform 5 on a map that identifies any of the public safety agency's jurisdictions, the geographic subject to the query, and registrant profiles that match the query criteria.

The data interpretation and exchange module 5 also implements the bilateral pointcaster 32, which includes an outbound communicator and an inbound communicator.

The outbound communicator initiates an outbound registrant notification to one or more registrants, via any of the communications methods registered within the each registrant's profiles stored with the registrant information 18.

The inbound communicator provides a way to receive messages indicating whether an expected action has been taken in connection with a registrant having a particular profile. The response state may, for example, indicate whether an emergency responder was able to check in on a particular registrant, or whether a registrant identified through a query made by the business intelligence platform 5 actually responded to an outbound notification, and if so, what the response indicated about the ultimate disposition of that registrant, for example whether the registrant has taken refuge in a shelter, with relatives.

Finally, the data interpretation and exchange module 5 provides an export module for exporting data returned by a business intelligence platform query for use by a system outside of the emergency management information system 10. Such output can be in any electronic form, including but not limited to XML files (such as CAP), formatted data extracts, and datasets compatible with the emergency management information system 10. This exported data can be used to support further off-line interpretation, analysis, visualization, or storage.

Having described the invention, and a preferred embodiment thereof, what we claim as new and secured by Letters Patent is:

1. An apparatus for management of information for use in mitigating an emergency, said apparatus comprising a data storage device configured to store registrant information obtained from members of a population residing in a particular geographic area, and a set of survey questions, and a data storage system, said data storage system configured to implement a survey editor, said survey editor being configured to enable emergency management agencies to create a survey for soliciting, from said members, information for inclusion in said registrant information, wherein said information is pertinent to planning for, mitigating, responding to, or recovering from said emergency, said survey editor providing, to said emergency management agencies, an interface corresponding to each agency, said interface being configured to enable selection of a subset of questions from said set of questions, said subset of questions being selected from said set of questions based at least in part on said particular geographic area, and a survey portal, said survey portal being configured to enable receipt, from said member, of a response to said survey, wherein said data storage system is further configured to integrate said response into said registrant information.

2. The apparatus of claim 1, wherein said data storage system is further configured to implement a business intelligence platform configured to receive instructions from an emergency management agency, said instructions, when executed by said business intelligence platform, causing identification of a subset of said registrant information based at least in part on a registrant profile that includes a geographic location, and causing retrieval of said subset of said registrant information.

3. The apparatus of claim 2, wherein said business intelligence platform is configured to inspect credentials of said emergency management agency and to control access to said registrant information based at least in part on said credentials.

4. The apparatus of claim 1, wherein said data storage system is further configured to implement a pointcaster configured to send emergency messages to selected members of said population based on both geographic location of said members as specified in said registrant information and matching an element of the subset of questions being selected.

5. The apparatus of claim 4, wherein said pointcaster is further configured to receive response messages from said selected registrants in response to said emergency messages.

6. The apparatus of claim 1, wherein said data processing system is further configured to provide access to said registrant information to a call-taker of a 9-1-1 call.

7. The apparatus of claim 6, wherein said data processing system is further configured to restrict access to selected portions of said registrant information based at least in part on credentials of said call-taker.

8. The apparatus of claim 1, wherein said survey editor comprises an interface, said interface being configured to enable receipt of a free-form question and including said free-form question in said survey with said subset of questions.

9. The apparatus of claim 1, wherein said survey editor comprises an interactive map interface configured to enable receipt, from said emergency management agency, of a graphical representation of said particular geographic area.

10. The apparatus of claim 1, wherein said survey editor is further configured to inspect credentials of said emergency service agency and to restrict survey editing by said emergency service agency based at least in part on said credentials.

11. The apparatus of claim 2, wherein said business intelligence platform comprises an interactive map interface configured to enable receipt, from said emergency management agency, of a graphical representation of said particular geographic area.

12. The apparatus of claim 1, wherein said emergency is a result of a terrorist attack.

13. The apparatus of claim 1, wherein said data processing system is configured to interact with a first emergency management agency and with a second emergency management agency, and wherein said data processing system is further configured to deny access to selected registrant information to said first emergency management agency and to grant access to said selected registrant information to said second emergency management agency.

14. The apparatus of claim 1, wherein said data storage system is further configured to implement a pointcaster configured to send emergency messages to selected members of said population based on both geographic location of said members as specified in said registrant information and satisfaction of a survey criterion.

15. A method for collecting information to be used for mitigating an emergency, said method fully carried out by a computing device, said method comprising configuring a data storage device to store registrant information obtained from members of a population residing in a particular geographic area, and a set of survey questions, and configuring a data storage system to implement a survey editor, said survey editor being configured to enable emergency management agencies to create a survey for soliciting information from said members of said population residing in said particular geographic area, said information being information that is pertinent to planning for, mitigating, responding to, or recovering from said emergency, said survey editor providing, to said emergency management agencies, an interface corresponding to each agency, said interface being configured to enable selection of a subset of questions from said set of questions, using said survey editor, selecting a subset of questions from said set of questions based at least in part on said particular geographic area, and receiving, from a member of said population, via a survey portal, a response to said survey, and integrating said response into said registrant information.

16. The method of claim 15, further comprising including a free form question in said subset of questions.

17. The method of claim 15, further comprising, in response to occurrence of an emergency, sending a message to members of said community based on geographic location of said members and on an extent to which said members satisfy selected survey criteria.

* * * * *